US010866237B2

(12) United States Patent
Paek

(10) Patent No.: US 10,866,237 B2
(45) Date of Patent: Dec. 15, 2020

(54) ULTRAHIGH-SENSITIVITY TWO-DIMENSIONAL CHROMATOGRAPHY-BASED BIOSENSOR

(71) Applicant: Korea University Research and Business Foundation, Seoul (KR)

(72) Inventor: Se-Hwan Paek, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 239 days.

(21) Appl. No.: 15/416,299

(22) Filed: Jan. 26, 2017

(65) Prior Publication Data
US 2017/0241962 A1    Aug. 24, 2017

(30) Foreign Application Priority Data

Feb. 18, 2016    (KR) .................. 10-2016-0019212

(51) Int. Cl.
*G01N 33/558*    (2006.01)
*G01N 33/48*    (2006.01)
*G01N 21/84*    (2006.01)

(52) U.S. Cl.
CPC .......... *G01N 33/558* (2013.01); *G01N 33/48* (2013.01); *G01N 21/8483* (2013.01)

(58) Field of Classification Search
CPC ........ B01L 2300/0825; G01N 21/8483; G01N 33/558
See application file for complete search history.

(56) References Cited

U.S. PATENT DOCUMENTS

| 7,189,522 B2 * | 3/2007 | Esfandiari | ............ G01N 33/538 422/423 |
| 2006/0205059 A1 * | 9/2006 | Esfandiari | ............ G01N 33/538 435/287.2 |
| 2013/0129580 A1 * | 5/2013 | Flavin | .................. B01L 3/5023 422/501 |
| 2015/0361487 A1 * | 12/2015 | Bishop | ..................... B01L 7/00 435/6.12 |

FOREIGN PATENT DOCUMENTS

| KR | 10-2004-0092255 A | 11/2004 |
| KR | 10-2004-0093048 A | 11/2004 |
| KR | 10-2006-0009665 A | 2/2006 |

(Continued)

OTHER PUBLICATIONS

Cho et al. (Anal. Chem. vol. 78, pp. 793-800 (2006).*

(Continued)

*Primary Examiner* — Jill A Warden
*Assistant Examiner* — Dwayne K Handy
(74) *Attorney, Agent, or Firm* — Mintz Levin Cohn Ferris Glovsky and Popeo, P.C.; Steven M. Jensen; Joohee Lee

(57) ABSTRACT

Disclosed is an ultrahigh-sensitivity two-dimensional chromatography-based biosensor, wherein cross-flow of high driving force across a narrow membrane is applied, thereby enabling the elimination of background noise, efficient supply of a large-sized polymeric or high-molecular-weight signal tracer, sequential material supply for increased reactivity, and simultaneous washing and signal generation when additional signal generation is required, as in an enzyme.

11 Claims, 11 Drawing Sheets

(56) References Cited

FOREIGN PATENT DOCUMENTS

KR 10-1111968 B1 2/2012

OTHER PUBLICATIONS

Park, Joonhyuck et al., "Signal Amplification via Biological Self-Assembly of Surface-Engineered Quantum Dots for Multiplexed Subattomolar Immunoassays and Apoptosis Imaging", ACS NANO (2013) pp. 9416-9427.

Lim, Guei-Sam et al., "Chemiluminometric Immunosensorfor High-Sensitivity Cardiac Troponin I Employing a Polymerized Enzyme Conjugate as a Tracer", Scientific Reports (2015) pp. 1-11.

Bassand, Jean-Pierre et al., "Guidelines for the diagnosis and treatment of non-ST-segment elevation acute coronary syndromes", European Heart Journal (2007) 28, pp. 1598-1660.

Seo, Sung-Min et al., "A fluorescent immunosensor for high-sensitivity cardiac troponin I using a spatially-controlled polymeric nano-scale tracer to prevent quenching", Biosensors and Bioelectronics, 83 (2016) pp. 19-26.

* cited by examiner (A) Stepwise polymerization:

(B) Post-refinements:

(A) FE-SEM image of fluorescently-labeled antibody in nano-scale

One-step reaction     Two-step reaction     Five-step reaction (B) Size distribution of fluorescently-labeled antibody (A) Image of cartridge components (B) Image of assembled cartridge with strip, pouch, and absorption pad (C) Portable fluorescence detection device

ULTRAHIGH-SENSITIVITY TWO-DIMENSIONAL CHROMATOGRAPHY-BASED BIOSENSOR

CROSS REFERENCE TO RELATED APPLICATION

This application claims the benefit of Korean Patent Application No. KR 10-2016-0019212, filed Feb. 18, 2016, which is hereby incorporated by reference in its entirety into this application.

TECHNICAL FIELD

The present invention relates to a technique for improving signal amplification performance of a biosensor in a variety of analytical fields, including biomedical diagnosis fields requiring ultrahigh-sensitivity analysis, which is a technique pertaining to large-sized signal tracer supply, background noise signal control and signal generation, based on two-dimensional chromatography at the time of performing a bioassay.

BACKGROUND ART

In order to realize high-sensitivity diagnosis in diagnostic testing fields, the technique of the present invention enables polymeric or high-molecular-weight materials for signal amplification to be applied without limitation to membrane-based point-of-care (POC) biosensors. Compared to conventional membrane-based POC products using polymeric signal tracers and high-molecular-weight large-sized signal tracers, the technique of the invention has the following advantages: first, any type of signal tracer may be supplied without limitation through a variety of supply routes; second, a background noise signal may be eliminated through washing, enabling to overcome the generation of the background noise signal via a nonspecific reaction and difficulty in supplying a large-sized signal tracer; and third, signal generation proportional to the concentration of an analyte may be performed at the same time as washing, as necessary, thus increasing a signal-to-noise ratio to thereby ensure competitiveness and technical excellence in the market thanks to the use of various signal tracers.

Conventionally, many attempts have been made to improve signal tracers for signal amplification in order to increase biosensor sensitivity. For fluorescent signal tracers, fluorophores having superior quantum yields are synthesized to obtain stronger emission signals, or multiple fluorophores are polymerized to a predetermined backbone such as a dendrimer, thereby increasing the number of fluorophores that are supplied. Here, in the case where a polymeric fluorophore is synthesized to increase the number of fluorophores, when the distance between the fluorophores is decreased to 10 nm or less, self-quenching occurs due to energy transfer, in which excited internal electron energy is transferred to a neighboring fluorophore without the emission of photons and the electrons thus enter a ground state, undesirably resulting in signal loss. Accordingly, thorough research is ongoing into signal amplification through an improvement in fluorophore molecule array, such as a fluorophore chain obtained by connecting fluorophores at a predetermined interval to a dendrimer, fluorescent beads configured such that fluorophores are attached to large-sized beads at a predetermined interval, a fluorescence resonance energy transfer (FRET)-induced fluorophore chain through reverse use of energy transfer by connecting two kinds of fluorophores as a donor and an acceptor, and a polymeric fluorophore, and thus large-sized fluorescent polymeric or high-molecular-weight signal tracers have been developed. In the case of typically useful metal nanoparticles such as colloidal gold, signal amplification has been studied by increasing the size in a manner in which large metal nanoparticles having a size of 40 nm are coated with small particles having a size of 10 nm. In this case, a metal nanoparticle cluster comprising nanoparticles having different sizes is large and thus makes it difficult to flow using capillary action, and limitations are imposed on supplying such a signal tracer all at once to a POC biosensor membrane. For this reason, sequential supply, in which large particles are first reacted and small particles are then reacted, is currently available in POC biosensors.

In the case of a polymeric signal tracer using an enzyme, the strength of a provided signal is in proportion to an increase in the amount of enzyme for generating a signal, and thus, when a polymeric enzyme signal tracer, in which enzymes are bundled together, is supplied all at once, an amplified signal may be ensured, but such a polymeric signal tracer, having a large size, is difficult to supply to a POC biosensor using capillary action. The surface area of the membrane is much larger than a typical plastic plate (e.g. 100 times or more), and the biosensor is manufactured in the form of a long strip in which the length of the membrane is greater than the width thereof, whereby the travel distance of the signal tracer is increased upon lateral flow-based analysis. As the interaction of the large-sized signal tracer with the surface of the membrane is remarkably increased, a non-specific reaction increasingly occurs, making it difficult to supply the large-sized signal tracer.

Although the aforementioned techniques are used to amplify the signal of the biosensor by increasing the number and size of various signal tracers, such as fluorophores, beads, enzymes, metal nanoparticles, fiber beads, etc., when such large-sized polymeric or high-molecular-weight signal tracers are applied in practice to membrane-based POC biosensors, background noise may be generated with an increase in the nonspecific reaction due to the large size of the polymeric or high-molecular-weight signal tracer, and a large-sized signal tracer is difficult to supply using the capillary action in the membrane.

SUMMARY

Accordingly, the present invention has been made keeping in mind the above problems encountered in the related art, and the present invention is intended to provide a biosensor and an analysis method using the same, wherein the biosensor is able to control noise and the supply of a signal tracer, and enables signal generation. In the present invention, various kinds of polymeric or high-molecular-weight signal tracers, such as fluorophores, beads, enzymes, metal nanoparticles, and fiber beads, which have been conventionally developed, may be utilized as signal generation materials for POC biosensors. Although conventional biosensors are problematic because background noise signals may be generated due to nonspecific reactions and it is difficult to supply large-sized polymeric or high-molecular-weight signal tracers, two-dimensional chromatography, in which fast cross-flow is induced through a narrow-width region across the POC biosensor membrane, is applied, whereby the background noise signal in the nonspecific reaction is eliminated through washing, and the large-sized polymeric signal tracer is sequentially supplied through cross-flow, as necessary. In the case of a signal tracer that requires an additional signal generation procedure, such as an enzyme, a signal may be generated by supplying a substrate or by using a substrate solution as a washing solution at the same time as washing, whereby a variety of high-sensitivity polymeric or high-molecular-weight signal tracers, the conventional use of which is limited, may be applied to membrane-based POC biosensors, ultimately remarkably increasing the sensitivity of the biosensor.

The present invention provides a biosensor and an analysis method using the same. Here, various kinds of polymeric or high-molecular-weight signal tracers, such as fluorophores, beads, enzymes, metal nanoparticles, and fiber beads, can be utilized as signal generation materials. Furthermore, through two-dimensional chromatography, in which fast cross-flow is generated through a narrow-width region across the POC biosensor membrane, the background noise signal in the nonspecific reaction is eliminated through washing, and the large-sized polymeric or high-molecular-weight signal tracer is sequentially supplied through cross-flow, as necessary. In the case of a signal tracer that requires an additional signal generation procedure, such as an enzyme, a signal can be generated by supplying a substrate at the same time as washing, whereby a variety of high-sensitivity polymeric or high-molecular-weight signal tracers, the conventional use of which is limited, can be applied to membrane-based POC biosensors.

A membrane-based POC biosensor is a device for generating a signal in proportion to the concentration of an analyte through biological, immunological and chemical reactions while allowing a target material and any type of analyte to flow together using, as flow driving force, lateral fluid flow using capillary action generated from a thin long membrane strip. However, since this flow is not fast, the physical flow driving force thereof is not sufficient to remove the signal tracer nonspecifically attached to the surface of a membrane or to supply a large-sized polymeric or high-molecular-weight signal tracer, the flow of which is not efficient. The cross-flow across the thin long membrane moves along a narrow-width region, and thus physically results in a fast flow rate. Using such a fast flow rate, signal tracers nonspecifically attached to the surface of the membrane are washed, and a large-sized polymeric or high-molecular-weight signal tracer can be efficiently supplied through cross-flow, as necessary, and also sequential material supply for increased reactivity is possible. Thereby, the conventional problems can be solved as follows: a background noise signal, which is undesirably generated when using a large-sized polymeric or high-molecular-weight signal tracer, can be minimized through washing, and the large-sized polymeric signal tracer, which is difficult to efficiently supply, can be supplied using high driving force of cross-flow.

Accordingly, two-dimensional chromatography can be utilized 1) for washing a noise signal using fast flow driving force, 2) for efficiently supplying a large-sized polymeric or high-molecular-weight signal tracer through fast fluid power and a short distance, which is the narrow width of the membrane, 3) for sequential material supply for increased reactivity, as necessary, and 4) for supplying a substrate for generating a signal at the same time as washing in the case where additional signal generation is required, as in an enzyme.

When this technique is utilized, washing efficiency and material supply efficiency can be further improved, compared to conventional washing or substrate supply methods including sample introduction and additional introduction of a solution from the back of the sensor. In the conventional additional supply method from the back, since the secondary solution is supplied through the same route under the condition that the membrane is already wet through sample supply, the capillary force is weak, making it difficult to effectively eliminate the background noise signal and to efficiently supply the large-sized polymeric or high-molecular-weight signal tracer.

With the goal of solving conventional problems, the structure of a membrane-based POC biosensor is improved so as to generate cross-flow across the narrow-width region of the membrane without the use of additional external power, thereby 1) ensuring a stable background signal through noise signal control using washing, 2) developing various biosensors suitable for purposes and end uses through application of a variety of polymeric or high-molecular-weight signal tracers regardless of the size thereof and through sequential material supply for increased reactivity, and 3) realizing high-sensitivity signal generation through substrate supply at the same time as washing in the case of a polymeric enzyme signal tracer requiring additional signal generation, ultimately enabling early diagnosis and ultralow-concentration analysis on site in biomedical diagnostic testing and analytical fields using various signal types (fluorescent, colorimetric, luminescent, electrical, thermal, magnetic signals, etc.).

When the polymeric or high-molecular-weight signal tracer is applied in practice to a membrane-based POC biosensor using cross-flow, analytical sensitivity is increased at least ten times compared to the case of using a cross-flow biosensor including an existing low-molecular-weight signal tracer (having a molecular weight of 500,000 or less, or a diameter of less than 100 nm). For example, in the case where cardiac troponin I, which is a specific biomarker for diagnosing acute myocardial infarction, is measured, analytical sensitivity is 50 to 100 pg/mL (Jung-Hwan Cho et al., Journal of chromatography B, 967, 139-146, 2014) when using the existing low-molecular-weight signal tracer, but is increased to the level of 2 to 7 pg/mL when using the polymeric or high-molecular-weight signal tracer (Biosensors and Bioelectronics, 83, 19-26, 2016). The reason why the analytical sensitivity is increased using the polymeric or high-molecular-weight signal tracer is that noise signal control through washing and sequential material supply are possible and also that washing and substrate supply can be carried out simultaneously in the case where additional signal generation is required, as in the case of an enzyme.

The effect of the polymeric or high-molecular-weight signal tracer is difficult to realize in conventional biosensors, most of which depend only on one-dimensional vertical flow. This is because it is difficult to control nonspecific signal generation due to the supply of a large-sized signal tracer and limited washing. In a conventional method for overcoming this problem, the signal tracer is merely used at low concentration. Even when the polymeric or high-molecular-weight signal tracer is applied to the one-dimensional flow-based biosensor, the results are similar to those obtained when using the low-molecular-weight signal tracer.

DETAILED DESCRIPTION

Figure 1:
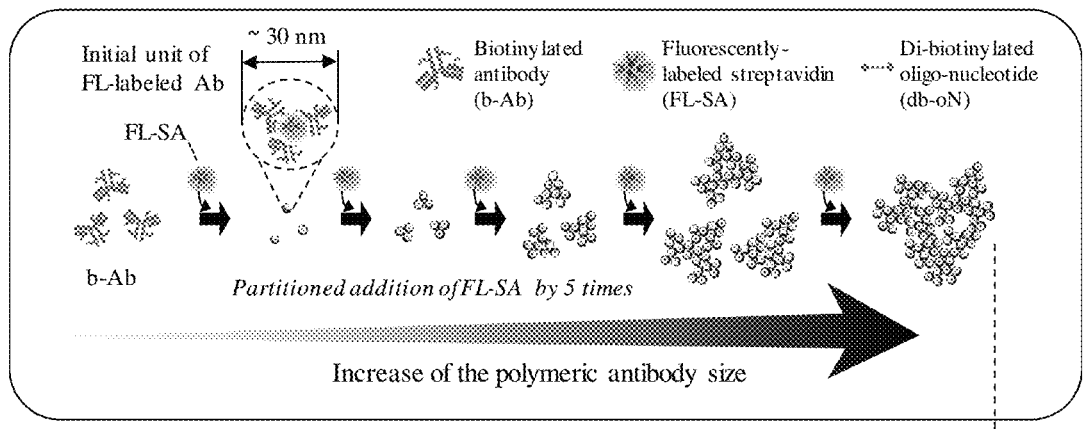
FIG. 1 shows the preparation of a polymeric fluorescent signal tracer.
Figure 1:
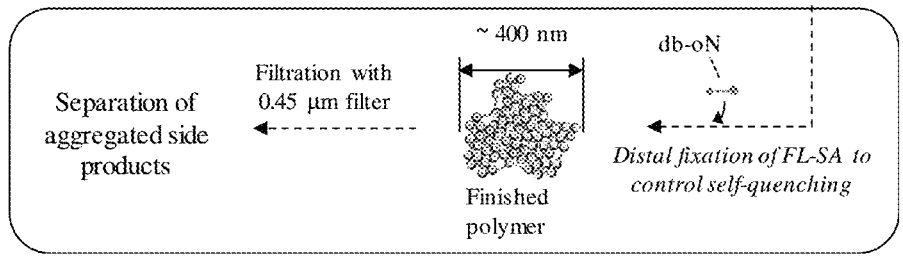

The present invention pertains to a two-dimensional chromatography-based biosensor comprising a vertical supply channel and a horizontal supply channel, and particularly to a biosensor and an analysis method using the same, wherein cross-flow of great driving force across a narrow membrane is used, thereby enabling the elimination of a background noise signal due to a large-sized polymeric or high-molecular-weight signal tracer, sequential material supply for increased reactivity, and simultaneous washing and signal generation when additional signal generation is required, as in an enzyme. When the cross-flow technique is applied to a membrane-based POC biosensor, a polymeric or high-molecular-weight signal tracer of any type (colorimetric, luminescent, fluorescent, electrical, thermal, magnetic signals, etc.) that enables signal amplification may be utilized as the signal generation source of a membrane-based POC biosensor that causes lateral flow, thus enabling noise control, signal tracer supply control, and signal generation, as necessary.

The biosensor of the present invention may include a capturing element for an analyte in a sample, which is immobilized on a porous membrane, and a detection element comprising a polymeric or high-molecular-weight large-sized signal tracer, which detects the reaction of the analyte and the capturing element, and the vertical supply channel may be used to react the analyte with the capturing element.

The horizontal supply channel may be configured such that noise is eliminated through washing of remnants after the reaction of the polymeric or high-molecular-weight large-sized signal tracer used as the detection element in the vertical supply channel, and the polymeric or high-molecular-weight large-sized signal tracer is sequentially supplied and controlled.

The horizontal supply channel may be used to supply a substrate solution when signal generation is additionally required.

The polymeric or high-molecular-weight large-sized signal tracer is a material having a molecular weight of 500,000 or more or having a size of 100 nm or more, and the polymeric or high-molecular-weight large-sized signal tracer may include a labeling material for signal generation, having a linker, so as to realize direct polymerization with a detection sensitive component or post-polymerization.

The linker may be formed through a biological reaction such as a biotin-streptavidin binding, an antigen-antibody binding, a nucleotide reaction, or a ligand-binder interaction, or through chemical bonding.

The detection element may include, but is not limited to, at least one selected from among an antibody, enzyme, receptor, DNA, RNA, PNA, protein, carbohydrate, inorganic material and ion, each of which specifically reacts with the analyte.

The labeling material for signal generation is able to generate a fluorescent, colorimetric, luminescent, electrochemical, thermal or magnetic signal, which may be generated alone or in combination by repeatedly using the labeling material.

Specifically, fluorescence uses a fluorescent material. When the fluorescent material is irradiated with light at a specific wavelength, internal electron energy enters an excited state and is then turned into a ground state while photons are emitted at a specific wavelength. Here, the photons emitted at a specific wavelength are detected using a fluorescent scanner. A colorimetric process uses nanometer- to micrometer-sized color particles (gold particles, latex beads, etc.) or an enzyme, and examples of the enzyme may include HRP (Horseradish Peroxidase) and ALP (Alkaline Phosphatase). When TMB (Tetramethylbenzidine) or DAB (Diaminobenzidine) in the case of the HRP enzyme or NBT (NitroBlue Tetrazolium) in the case of the ALP enzyme is supplied as a substrate, the substrate is decomposed by the enzyme to give a chromogenic enzyme product, which is then measured for absorbance and intensity at a specific wavelength. Luminescence, especially chemiluminescence also uses an enzyme. In this case, a luminol substrate is supplied to prepare a luminescent enzyme product, and the light intensity is measured. An electrochemical process is performed in a manner in which a biospecific reagent (enzyme, antigen, antibody, biochemical material, etc.) is immobilized on the surface of an electrode or is contained therein, whereby a biological recognition phenomenon is measured in the form of quantitative current, conductivity or potential. In the case of a thermal signal, an endothermic or exothermic state is detected using a thermistor, which is a kind of a physical sensor, and is then converted into an electrical signal for measurement, or a biospecific reagent (enzyme, antigen, antibody, biochemical material, etc.) is used, so that a biological recognition phenomenon is measured through changes in resistance or heat generation. In the case of a magnetic signal, changes in magnetic field are measured, and a complementary target molecule or probe molecule is attached to a large number of magnetic labels (magnetic particles or beads), thereby detecting a stray magnetic field of the magnetic label remaining around the sensor. These signal measurement methods may be appropriately modified or altered.

The capturing element may be at least one selected from among an antibody, enzyme, receptor, DNA, RNA, PNA and protein, each of which specifically reacts with an analyte or specifically reacts with a complex including an analyte.

The vertical supply channel may be configured such that a membrane pad for sample addition, a membrane pad for accumulating a large-sized signal tracer obtained by polymerizing a detection element and a labeling material for signal generation, a membrane pad for signal generation on which the capturing element is immobilized, and a membrane pad for absorbing a vertical flow solution are sequentially disposed upwards. The membrane pads, which are disposed adjacent to each other, may be configured such that they are partially overlapped to continuously induce capillary action through the membrane pores. This configuration is advantageous because a sample passes through pads having different functions during movement through lateral flow using the capillary action, whereby individual immunoassay processes are automatically carried out.

Specifically, when a sample is introduced into the membrane pad for sample addition, a capillary force is induced by the membrane pad for absorbing a vertical flow solution, whereby the solution is moved in a vertical direction by means of the above force. Then, the sample introduced into the membrane pad for sample addition is moved to the next membrane pad for accumulating a large-sized signal tracer obtained by polymerizing a detection element and a labeling material for signal generation, whereby the analyte is reacted with the large-sized signal tracer obtained by polymerizing the detection element and the labeling material for signal generation. Subsequently, the sample is moved to the next membrane pad by means of the capillary force for signal generation on which the capturing element is immobilized, whereby the analyte bound to the large-sized signal tracer obtained by polymerizing the detection element and the labeling material for signal generation is captured by the capturing element that is immobilized and thus stays on the membrane pad, whereas the remaining material, which is not captured, is continuously moved up to the membrane pad for absorbing a vertical flow solution by means of the capillary force. After the completion of the lateral flow in this way, when the analyte to be detected is present on the membrane pad for signal generation, it is left behind on the surface of the membrane in a state of being captured with the large-sized signal tracer, and thus, the presence or absence thereof may be checked by measuring the signal through the aforementioned processes using various signal generation materials. When the vertical supply channel is configured as mentioned above, the immunoassay reaction may be automatically, rapidly, and conveniently carried out through the flow of the added sample.

The horizontal supply channel may include, upon analysis, a membrane pad for supplying a washing solution to wash the remnants left behind in the vertical supply channel and a membrane pad for absorbing a horizontal flow solution, or may include, upon the supply of a large-sized signal tracer, a membrane pad for supplying a signal tracer solution to control the sequential supply thereof through the horizontal supply channel as an alternative to supply using the vertical supply channel, and a membrane pad for absorbing a horizontal flow solution. Furthermore, it may include, when additionally requiring signal generation, a membrane pad for supplying a substrate solution and a membrane pad for absorbing a horizontal flow solution.

The horizontal supply channel may be configured such that the washing solution, the signal tracer solution, the solution for signal amplification, and the substrate solution may be separately supplied, or at least two solutions thereof may be simultaneously or sequentially supplied.

When the solution is supplied through the horizontal supply channel, horizontal flow may be formed by partially overlapping and fixing the membrane pad for solution supply and the membrane pad for absorbing a horizontal flow solution at each lateral side of the membrane pad for signal generation of the vertical supply channel.

The pads of the horizontal supply channel may be first fixed on the membrane pad for signal generation coupled with the pads of the vertical supply channel, or may be first separated and then fixed after the completion of the reaction of the analyte with the large-sized signal tracer and the capturing element through the longitudinally configured pads, whereby washing, signal tracer supply control, and signal generation may be implemented through the introduction of the washing solution, the signal tracer solution, the solution for signal amplification, and the substrate solution, respectively.

When the horizontal supply channel is configured, the horizontal flow may be induced by introducing the solution in the presence of the membrane pad for absorbing a horizontal flow solution attached to one lateral side thereof, without the membrane pad for solution supply at the other side thereof.

When the solution is introduced in order to induce the horizontal flow, the solution may be manually introduced, or the solution may be introduced by breaking a tank containing the solution at the upper position or the side position on the membrane pad for solution supply.

In addition, the present invention addresses a method of analyzing an analyte using the biosensor. The analysis method of the present invention may include the steps of I) treating an analytical sample in a vertical supply channel containing a capturing element for an analyte, and II) supplying, as a washing buffer, a solution including either or both of a salt-containing buffer and a surfactant in order to supply the large-sized signal tracer to the horizontal supply channel or to eliminate a noise signal due to the large-sized signal tracer.

The salt-containing buffer may include, but is not limited to, physiological saline, phosphate saline, Tris saline, HEPES, or glycine saline.

EXAMPLES

A better understanding of the present invention may be obtained via the following examples, which are merely set forth to illustrate but are not to be construed to limit the scope of the present invention, and such examples may be appropriately modified and altered by those skilled in the art within the scope of the invention.

Test Materials

A stock of a cTn I-T-C complex (SRM 2912) and monoclonal antibodies specific to cTnI (clone M18, 560, 19C7, and MF4) were supplied from Hytest (Turku, Finland). Dibasic sodium phosphate, monobasic sodium phosphate monohydrate, sodium chloride, casein (in sodium salt form, extracted from milk), 3,3',5,5'-tetramethylbenzidine dihydrochloride (TMB), Sephadex G-15, and D-(+)-trehalose dehydrate were purchased from Sigma (St. Louis, Mo., USA). An NC film (HiFlowPlus HFB13504) and a polyester film were supplied from Millipore (Billerica, Mass., USA). EZ-Link NHS-LC-LC-biotin, succinimidyl 4-(N-maleimidomethyl)cyclohexane-1-carboxylate (SMCC), N-succinimidyl 3-(2-pyridyldithio)-propionate (SPDP), dithiothreitol (DTT), goat anti-mouse IgG, and SuperSignal West Femto chemiluminescent substrate for HRP were purchased from Thermo Fisher Scientific (Rockford, Ill., USA). Streptavidin and HRP were supplied from Calbiochem (San Diego, Calif., USA). A cellulose membrane (17CHR, chromatography grade) and a glass fiber membrane were obtained from Whatman (Maidstone, England) and MDI (Ambala Cantt, India), respectively. Hydrogen peroxide, insoluble TMB, and streptavidine-PolyHRP20 (SA-Poly-HRP) conjugate were obtained from Junsei (Tokyo, Japan), Moss (Pasadena, Md., USA), and Fitzgerald (North Acton, Mass., USA), respectively. All reagents that were used were of analytical grades.

<Example 1> Elimination of Background Noise Using Two-Dimensional Chromatography-Based Biosensor Test Example 1: Evaluation of Ultrahigh-Sensitivity Analysis Performance of Two-Dimensional Chromatography-Based Biosensor Using a Polymeric Fluorescent Signal Tracer In this Example, a two-dimensional chromatography-based immunosensor was used. Specifically, a myocardial infarction-specific marker (cardiac troponin I; cTnI) was mixed with human serum to thus reach a predetermined concentration. When the marker was detected using a polymeric fluorescent signal tracer in the two-dimensional chromatography-based immunosensor, whether concentration response performance was improved by eliminating background noise when washing was performed through the horizontal flow was evaluated.

1. Preparation and Characterization of Polymeric Fluorescent Signal Tracer

A polymeric fluorescent signal tracer was synthesized through gradual polymerization and post-refinement, which are uniquely devised in the present invention (FIG. 1).

Figure 2:
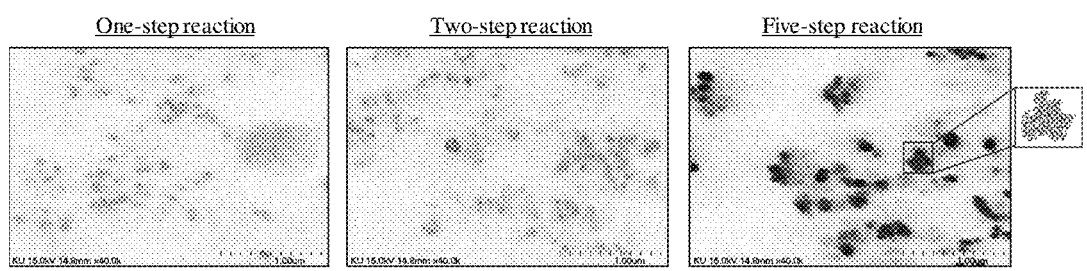
FIG. 2 shows images and a graph illustrating the characterization of the polymeric fluorescent signal tracer.
Figure 2:
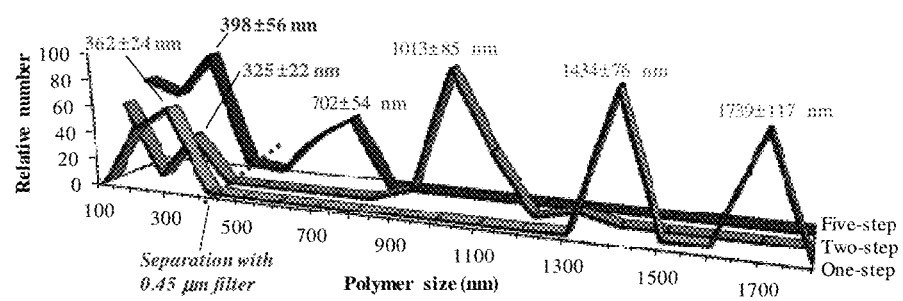

400 μg of cTnI-specific detection antibody was prepared in 100 μL of 140 mM NaCl-containing 10 mM phosphate, pH 7.4 (PBS). NHS-LC-LC-biotin at a 10-fold molar ratio to the antibody was dissolved in dimethyl sulfoxide (DMSO), and was then added to the detection antibody solution. This reaction was carried out at room temperature for 2 h with stirring at 800 rpm. After the completion of the reaction, the remaining reactive site was deactivated with the addition of 150 μL of 1 mol ethanolamine (pH 8.5). This conjugate was filtered through Sephadex G-15 gel filtration column (gel volume: 10 mL). The prepared conjugate was concentrated with VIVASPIN (molecular weight: 10,000), and then stepwise reacted with fluorescently labeled streptavidin. The biotinylated detection antibody and the fluorescently labeled streptavidin were added at a molar ratio of 1:1.25. In order to minimize the production of side products having undesired sizes, fluorescently labeled streptavidin (4.03 pmol) was stepwise added five times to the biotinylated detection antibody (3.224 pmol) with gentle stirring (800 rpm) at intervals (30 min). The relative spatial configuration therebetween was firmly fixed with spacing by a predetermined interval therebetween using di-biotinylated oligonucleotide. To ensure a polymeric fluorescent signal tracer having a predetermined size, the signal tracer was filtered using a 0.45 μm filter, centrifuged at 6,300 g for 3 min, and added with 3% ProClin 300 for long-term storage. The polymeric fluorescent signal tracer thus obtained was characterized using an electron microscope and a nanoparticle density meter, and the size of the signal tracer was determined to be about 400 nm (FIG. 2).

2. Manufacture of Two-Dimensional Chromatography-Based Biosensor

A two-dimensional chromatography-based immunosensor using the polymeric fluorescent signal tracer was manufactured as follows.

An immunosensor strip was configured such that four functional membrane pads were connected to each other so that they partially overlapped. The four functional membrane pads were a polyester pad (4×17 mm, Pall, Port Washington, N.Y.) for supplying a sample via a sample inlet, a glass fiber membrane pad (4×6 mm, Pall, Port Washington, N.Y.) for supplying a detection antibody and a polymeric fluorescent signal tracer, a nitrocellulose membrane pad (4×25 mm, HF180, EMD Millipore, Billerica, Mass.) for signal generation having a capture antibody immobilized thereon, and a cellulose chromatographic paper pad (4×15 mm, Whatman, Maidstone, UK) for absorption to induce fluid flow using capillary action, which were disposed upwards.

The polyester pad for sample supply was prepared by being immersed in PBS including 2% (weight/volume) bovine serum albumin (BSA) and 0.1% (volume/volume) Triton X-100 and then dried in an oven at 37° C. The glass fiber membrane pad for supplying a detection antibody and a polymeric fluorescent signal tracer was prepared in a manner in which the signal tracer comprising the detection antibody and the polymeric fluorescent signal tracer attached to each other was introduced into the glass fiber membrane pad so as to be supplied in an amount of 0.5 μg per strip, and then dried in an oven at 40° C. for 1 h. On the nitrocellulose membrane pad for signal generation, a capture antibody (clone 560; 0.5 mg/mL, including 0.1 trehalose) able to specifically detect a myocardial infarction-specific marker (cTnI, Hytest, Turku, Finland) was diluted with PBS and then dispensed at 0.7 μL/cm at the predesignated site for analyte. As a control group, anti-mouse IgG (0.2 mg/mL, including 0.1% trehalose) was dispensed at 0.7 μL/cm at the predesignated site for control. The pads thus prepared were aligned so that the ends thereof overlapped each other, fixed to a transparent plastic film using double-sided tape, and cut to a width of 4 mm, thereby manufacturing an immuno-strip.

Figure 3:
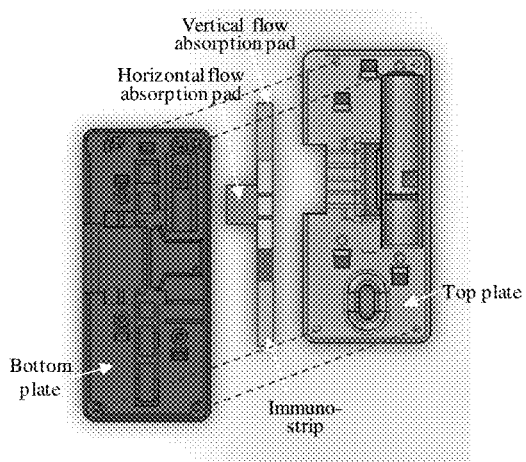
FIG. 3 shows the configurations of a two-dimensional chromatography-based biosensor system.
Figure 3:
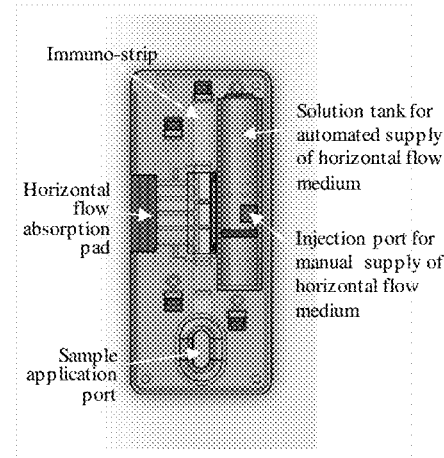
Figure 3:
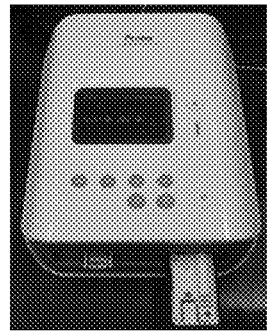
Figure 3:
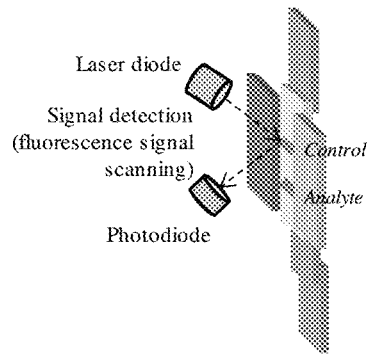

To manufacture a two-dimensional chromatography-based biosensor, the immunosensor strip manufactured above was mounted to a plastic cartridge comprising two top and bottom plates. Furthermore, to cause horizontal flow, two membrane pads for supply and absorption were disposed on each lateral side of the nitrocellulose membrane pad for signal generation of the immuno-strip such that they partially overlapped. In some cases, a horizontal flow solution tank for automatic supply was provided, or an inlet for manually supplying a horizontal flow solution was provided. The biosensor thus assembled was able to provide horizontal and vertical cross-flow channels upon immunoassay, and the fluorescent signal generated after the assay was measured using a fluorescent scanner (FIG. 3).

3. Elimination of Background Noise Due to Signal Tracer Using a Horizontal Flow Washing Effect Washing was performed through horizontal flow of the two-dimensional chromatography-based biosensor to eliminate the nonreactive background noise signal after the antigen-antibody reaction, and a 100 mM phosphate buffer (PB) containing 0.1% (volume/volume) Triton X-100 was used as a washing solution. The supply pad for supplying the washing solution was the glass fiber pad (16×13.4 mm, Pall, Port Washington, N.Y.), on which a 0.1% (volume/weight) BSA-containing 100 mM phosphate buffer (PB) solution was dispensed, and was provided by being dried in an oven at 37° C. for 1 h. The washing process was conducted in a manner in which 300 μL of the washing solution was supplied to the washing solution supply pad to induce horizontal flow.

In order to evaluate whether dose-response performance was improved by eliminating the background noise signal during the washing process, the case where the fluorescent signal was detected after only vertical flow by introducing the sample and the case where the fluorescent signal was detected after the washing process through the horizontal flow by introducing the washing solution were compared. To this end, the sample was prepared by diluting the myocardial infarction biomarker cTnI to concentrations of 0, 3.125, and 12.5 ng/mL with human serum (Sigma-Aldrich, Louis, Mo.), and was supplied via the sample inlet of the vertical channel.

In the experiment without the use of the washing process, the introduced sample was subjected to an antigen-antibody reaction for 15 min along the immuno-strip through the vertical flow, after which the fluorescent signal of the membrane for signal generation of the immuno-strip was measured using a fluorescent scanner. The fluorescent signal of the supplied sample was measured, and the concentration of the analyte corresponding to the measured value was substituted into the standard curve.

Meanwhile, in the experiment with the use of the washing process, the introduced sample was reacted for 15 min through the vertical flow, after which the washing solution was supplied to the solution supply pad of the horizontal channel. Then, cross-flow was induced across the membrane for signal generation of the immunostrip positioned between the two pads (the horizontal flow solution supply pad and the absorption pad for horizontal flow) of the horizontal channel, and the cross-flow was faster than the vertical flow and thus played a washing role in eliminating the nonreactive background noise signal (FIG. 4).

Figure 4:
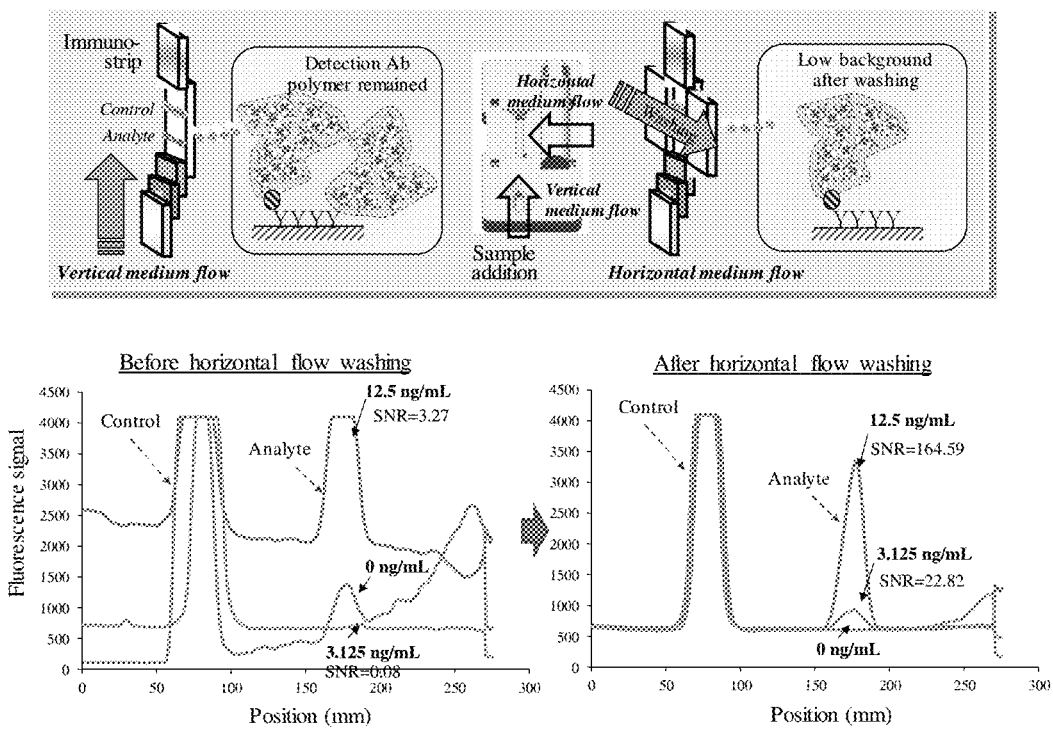
FIG. 4 shows the nonspecific reaction of the polymeric fluorescent signal tracer and the washing effect.

Thereby, the background noise, which occurred in the conventional membrane-based lateral-flow immunosensor using only the vertical flow, was attenuated in the washing process through the horizontal flow, and thus concentration response performance became superior (FIG. 4). Accordingly, the two-dimensional chromatography-based biosensor can be found to be suitable for ultrahigh-sensitivity analysis upon immunoassay.

4. Evaluation of Performance of Ultrahigh-Sensitivity Two-Dimensional Chromatography-Based Biosensor When the two-dimensional chromatography-based biosensor using the polymeric fluorescent signal tracer is applied upon immunoassay, the generated background noise can be eliminated to thus stabilize the background signal, thereby more clearly identifying the specific signal using the polymeric fluorescent signal tracer.

Figure 5:
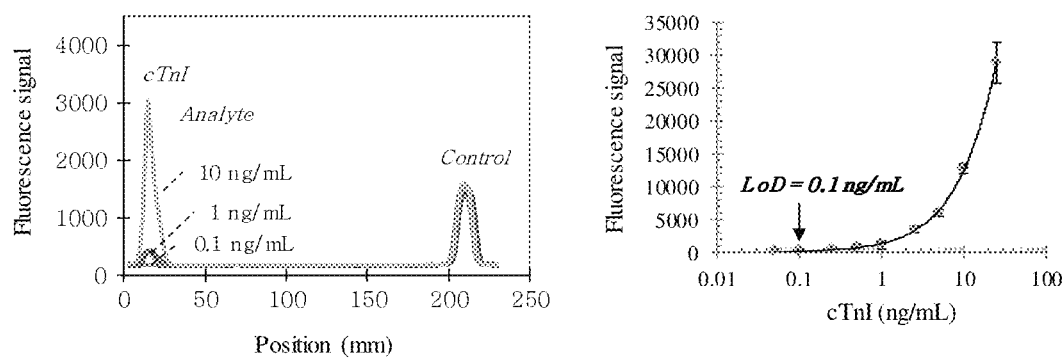
FIG. 5 shows graphs illustrating the concentration response performance of a biosensor using an existing low-molecular-weight fluorescent signal tracer.

For performance comparison, testing was first performed using an existing low-molecular-weight signal tracer. To synthesize the existing low-molecular-weight signal tracer, Alexa 647 fluorophore was polymerized at a 20-fold molar ratio to a detection antibody, and two-dimensional chromatographic immunoassay was performed for a cTnI standard sample in the concentration range of 0.05 to 50 ng/mL using the low-molecular-weight signal tracer thus obtained. Based on the results of the dose-response performance of the immunosensor using the existing low-molecular-weight signal tracer, the fluorescent signal was increased proportionally in the concentration range that was tested, but the analytical sensitivity thereof was only 0.1 ng/mL (FIG. 5). These results match those in a previous report (J. Chromatography B, 967, 139-146, 2014).

Figure 6:
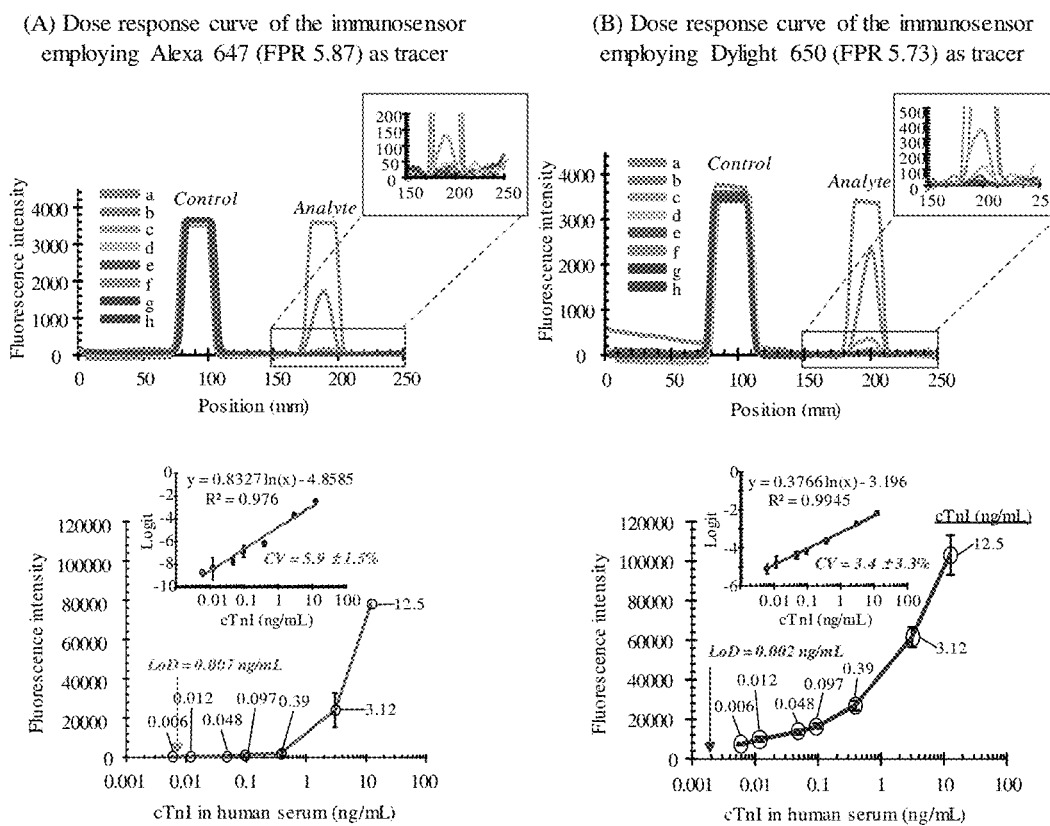
FIG. 6 shows graphs illustrating the high-sensitivity detection effects of the biosensor using the polymeric fluorescent signal tracer.

When the two-dimensional chromatography-based biosensor includes the polymeric or high-molecular-weight signal tracer, the background noise is eliminated and thus the specific signal in the low-concentration range is more clearly identified. To this end, additional testing was performed. The Alexa 647 polymeric fluorescent signal tracer was prepared through the processing as shown in FIG. 1, and cTnI was detected using the two-dimensional chromatography-based biosensor shown in FIG. 3. In this case, the analytical sensitivity (the lower measurement limit) was 0.007 ng/mL, which means that the low-concentration analyte was able to be sensitively measured (FIG. 6, (A)). In order to more definitively evaluate the ultrahigh-sensitivity measurement effect, a DyLight 650 polymeric fluorescent signal tracer was prepared, and the same testing was performed as above. As results thereof, the analytical sensitivity was 0.002 ng/mL, which means that cTnI was able to be detected at high sensitivity (FIG. 6, (B)).

Consequently, compared to when using the existing low-molecular-weight signal tracer, the two-dimensional chromatography-based biosensor using the polymeric signal tracer can be found to measure the analyte in the sample at a sensitivity increased at least ten times.

Figure 7:
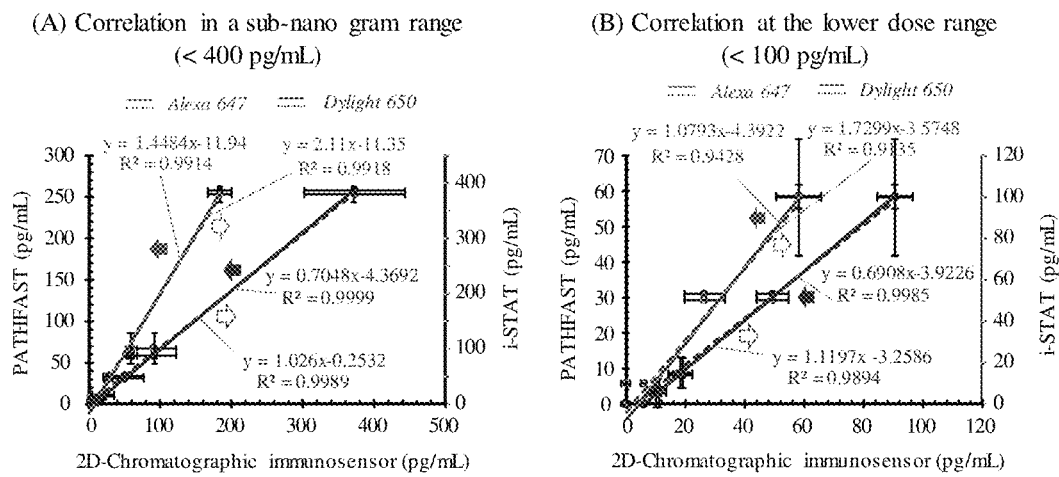
FIG. 7 shows graphs illustrating the correlations between the biosensor using the polymeric fluorescent signal tracer and a control device.

In the case where an existing polymeric signal tracer was used in the conventional lateral-flow immunosensor, the analytical results were not reproducible, owing to the irregular background noise generation. When the background noise present in the conventional immunosensor is washed through cross-flow, the background signal is stabilized to thus improve not only analytical sensitivity but also reproducibility of the analytical results. These results were compared with those of commercialized, expensive devices used for hospital diagnostic testing, for example, PathFast and i-STAT, and thus the correlation coefficient ($R^2$) in which the cTnI concentration exhibits a correlation in the range of less than a nanogram was measured and found to be 0.9955 on average for cTnI<0.4 ng/mL and 0.9610 for cTnI<0.1 ng/mL (FIG. 7). Accordingly, although the two-dimensional chromatography-based biosensor using the polymeric signal tracer can be manufactured at low cost, the detection capability was comparable to those of existing expensive devices as the correlation therewith was high even in a trace concentration range of cTnI.

Test Example 2: Evaluation of High Performance Through Control of Washing Frequency for Cross-Flow for Large-Sized Analyte The analyte in the sample, such as vesicles including plasma lipoprotein or exosome, had a size of about 30 to 150 nm, and the sample exhibited high viscosity in a concentrating process. In these materials, unlike different large-sized analytes, such as viruses, bacteria or molds, the number of identical epitopes recognized by the antibody was limited, and a monoclonal antibody that reacts with a specific epitope was used to maintain specificity.

In order to analyze large-sized analytes using the monoclonal antibody, an immunoassay, such as a microtiter plate-based enzyme-linked immunosorbent assay (ELISA), was utilized. Here, the antigen-antibody reaction time had to be remarkably prolonged (e.g. >4 hr). This is because the size of the analyte is large and the diffusion rate is decreased due to high viscosity of the concentrated sample, and thus the antigen-antibody binding occurs slowly on a solid phase. To more rapidly perform such analysis, an immunoassay using a membrane having a surface area at least 100 times as large, instead of the microtiter plate as the antibody immobilization matrix, may be employed. However, in the typical lateral-flow analysis using only primary vertical flow, the background noise is remarkably increased upon analysis of the large-sized analyte contained in the very viscous sample, making it difficult to perform high-performance immunoassay.

In this Test Example, when washing through cross-flow of the two-dimensional chromatography-based biosensor is appropriately utilized, the analyte that is large-sized and contained in a viscous sample may be subjected to rapid and superior immunoassay. To this end, this Test Example was performed in the same manner as Test Example 1, with the exception that the exosome was adopted as the analyte and the polymeric fluorescent signal tracer was produced by utilizing a monoclonal antibody specifically binding CD63 protein on the surface of the exosome as the detection antibody. The two-dimensional chromatography-based biosensor was manufactured in the same manner as in Test Example 1, with the exception that the monoclonal antibody for specifically detecting CD9 was immobilized as the capture antibody on the membrane for signal generation. The exosome was isolated from human blood through ultra-fast centrifugation, and two samples having standard concentrations of 0 and 100 μg were diluted with 50 mM Tris-HCl containing 0.5% casein and 0.1% Triton X-100.

Upon assay using the two-dimensional chromatography-based biosensor, 80 μL of the sample was introduced through a sample inlet of the biosensor and thereby subjected to an antigen-antibody reaction for 15 min along the immuno-strip through the vertical flow. Thereafter, an absorption pad for horizontal flow was mounted, a washing solution was supplied to induce the horizontal flow, and the reduction in background noise depending on the washing frequency was observed. In order to measure changes in signal depending on the number of washing processes, the biosensor cartridge was mounted in the fluorescent scanner to measure the fluorescent signal on the pad for signal generation of the immuno-strip.

Figure 8:
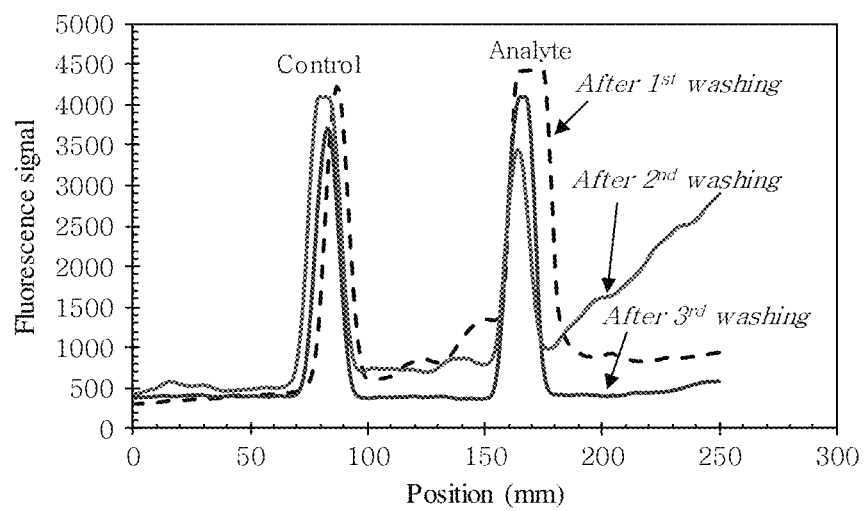
FIG. 8 shows a graph illustrating the improvement effect of concentration response performance of large-sized and viscous samples depending on washing frequency.

Based on the results of comparison of fluorescent signal depending on the washing frequency, as the number of washing processes was increased, the background noise was reduced, and a specific signal for the target exosome was observed to be different from the background noise (FIG. 8). Hence, upon measurement of the large-sized analyte in viscous sample, the horizontal flow is applied by controlling the number of washing processes, whereby immunoassay performance having high sensitivity and reproducibility can be found to result.

<Example 2> Control of Supply of Signal Tracer in Two-Dimensional Chromatography-Based Biosensor Test Example 1: Related Research for Introduction of Polymeric Enzyme Signal Tracer 1. Introduction Effect of Polymeric Enzyme Signal Tracer Upon Mitrotiter Plate-Based Immunoassay In order to use a polymeric enzyme signal tracer in immunoassay, the present inventors have adopted a microtiter plate as a matrix for immobilizing a capture antibody. Since the microtiter plate format is suitable for multiple analyses during the same time period, it was utilized in the initial process step of the present invention to test the effects of performance control factors. Particularly, a typical antigen-antibody sandwich reaction system (one-to-one binding format) using a single pair of capturing (clone 560) and detection (biotinylated clone 19C7) recognition materials was adopted. In the presence of the analyte cTnI in the sample, the sandwich immune complex including the enzyme signal tracer was formed and then further reacted with streptavidin (SA)-enzyme (horseradish peroxidase; HRP) polymeric signal tracer (SA-HRP), thus generating a signal proportional to the concentration of the analyte.

When the typical low-molecular-weight SA-HRP signal tracer, synthesized by crosslinking two different proteins, was introduced, the above analysis method exhibited a sensitivity of 0.9 ng/mL cTnI through quantitative measurement. This analysis performance is not sufficient for early diagnosis of acute myocardial infarction (AMI), requiring a 0.1 ng/mL clinical cut-off upon AMI onset.

Therefore, attempts have been made to improve analytical sensitivity by introducing the SA-chemically linked polymeric enzyme signal tracer (SA-Poly-HRP) for stoichiometric signal amplification, in lieu of the typical low-molecular-weight signal tracer. As results thereof, the detection sensitivity was increased to 0.05 ng/mL, and thus analysis performance was increased about 18 times. Furthermore, compared to when the typical signal tracer was used, the background noise was observed to be remarkably increased, which means that the polymeric signal tracer had a tendency to be nonspecifically attached in proportion to the molecular size.

2. Introduction Effect of Double-Sandwich Immune Complex Format

Since local necrosis of myocardial tissue may be a sign of reversible injury or AMI onset, high-sensitivity measurement for a specific marker such as hs-cTnI (high-sensitivity cTnI; cTnI<0.01 ng/mL) is regarded as important. cTnI is a marker for diagnosis and short-term prognosis of AMI patients, and is also a stable predictor of long-term prognosis in patients with coronary artery disease. In order to further improve immunoassay performance and to increase signal intensity, a double-pair sandwich immune complex was devised.

To this end, two pairs of monoclonal antibody combinations were selected using two capture antibodies (clones 560 and M18) and two biotinylated detection antibodies (clones 19C7 and MF4). In the case where immunoassay was performed using a typical low-molecular-weight SA-HRP signal tracer, detection performance was increased seven times when using the double-sandwich immune complex format compared to when using the single-sandwich format (0.13 ng/mL). When the SA-Poly-HRP was used as the polymeric signal tracer, analytical sensitivity was drastically increased 90 times (0.01 ng/mL) compared to the typical format. When the polymeric Poly-HRP signal tracer was used, the effect of the double-sandwich format was increased about five times compared to the single-pair format. Thus, the polymeric Poly-HRP signal tracer and the double-sandwich immune complex format were employed in the fabrication of the biosensor of the present invention.

Figure 9:
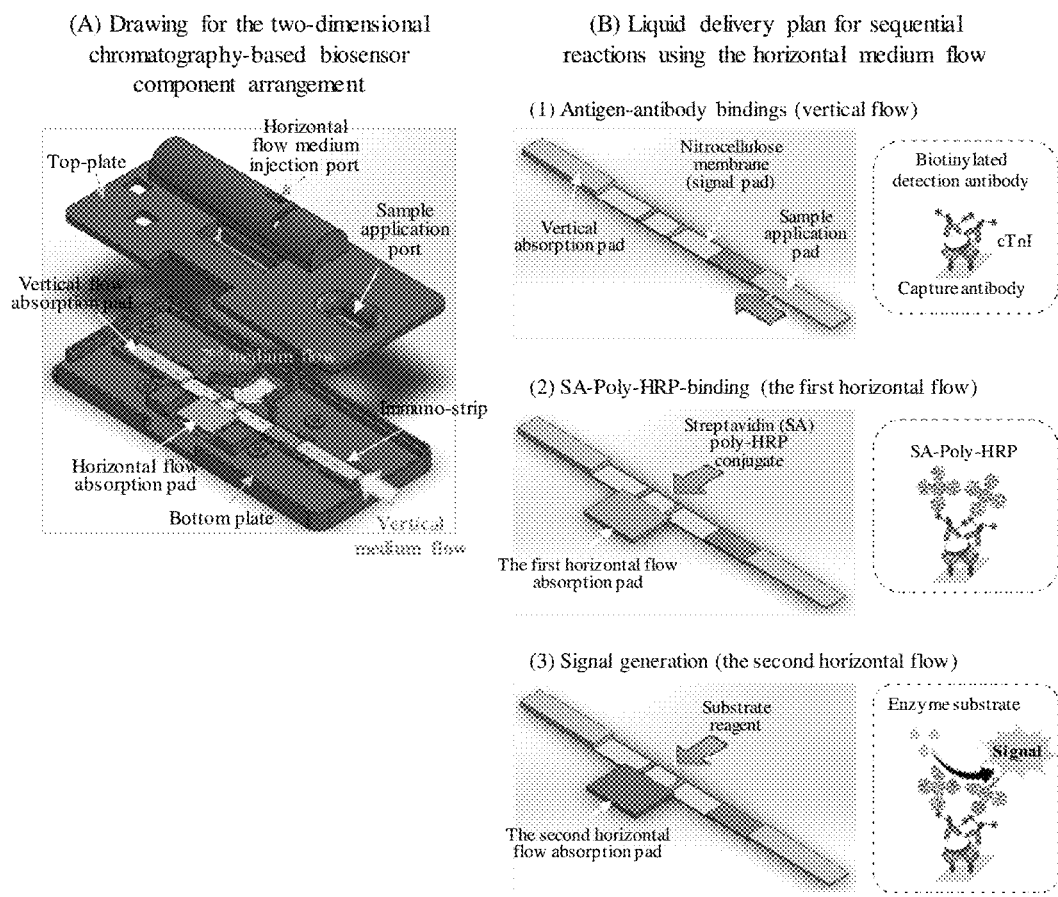
FIG. 9 shows the sequential supply control of the polymeric enzyme signal tracer.

Test Example 2: Control of Supply of Polymeric Signal Tracer Through Cross-Flow of Two-Dimensional Chromatography-Based Biosensor 1. Manufacture of Two-Dimensional Cross-Flow-Based Immunosensor In order to manufacture a functional immunosensor module, as shown in (A) of FIG. 9, the immuno-strip was provided to a plastic cartridge (33×76×12 mm) comprising top and bottom plastic plates. The bottom plate of the cartridge was composed of two cross-channels devised to vertically fix the immuno-strip and horizontally supply signal generation-related reagents (FIG. 9, (B)). The top plate was composed of a window for vertical signal monitoring, an inlet for sample supply, a reagent inlet oriented in a horizontal direction, and a partition for a horizontal flow absorption pad (FIG. 9, (A)). The above two plates were tightly assembled using a groove joint so that individual parts were maintained at respective positions.

2. Control of Supply of Polymeric Signal Tracer Using Two-Dimensional Chromatography In order to diagnose AMI on site, such as in an emergency room or an ambulance, the present inventors have manufactured a biosensor for rapid testing by using a membrane having a large surface area (e.g. 100 times that of a microwell) as a solid matrix. Although the large solid surface area may potentially cause high nonspecific attachment of the Poly-HRP signal tracer, nonspecific attachment may be controlled in the two-dimensional chromatography-based biosensor including the washing process through cross-flow. Also, the polymeric signal tracer has a large molecular size, undesirably causing steric hindrance upon immune sandwich binding with the capture antibody. Whether this potential limitation was able to be overcome through control of the supply of the polymeric signal tracer was tested.

Using the conventional process based on two-dimensional chromatography, the formation of a sandwich immune complex (FIG. 10, Process A of the upper panel) and Poly-HRP coupling through biotin-SA binding (FIG. 10, Process B) were simultaneously performed through vertical flow. In this experiment, a single-pair antibody was used. Subsequently, an enzyme substrate solution was added through horizontal flow across the signal pad (FIG. 10, Process C), thereby generating a colorimetric signal (a detail thereof will be described in Example 3 below), and the colorimetric signal, accumulated for 5 min, was quantified to thus be easily visualized. The colorimetric image was captured using a detector and digitized to obtain an optical density profile using a computer program. As expected, due to steric hindrance in the formation of the immune complex using a typical process, only 1 ng/mL cTnI in the sample was detected (FIG. 10, Co-reactions; see also the bar graph colored in red).

The analysis performance based on the control of the supply of the polymeric signal tracer via various sequential reaction routes was compared with that of the typical process. In order to improve the detection performance, the typical process was modified in a manner in which Processes A and B of FIG. 10 were separated so as to be sequentially carried out through vertical flow (FIG. 10; Sequential reactions, Scheme 1). The signal was generated in a horizontal flow mode, as in the typical method (Process C). As results thereof, the analytical sensitivity was increased at least ten times through sequential reactions of modified Scheme 1 (FIG. 10, the bar graph colored in purple).

Figure 10:
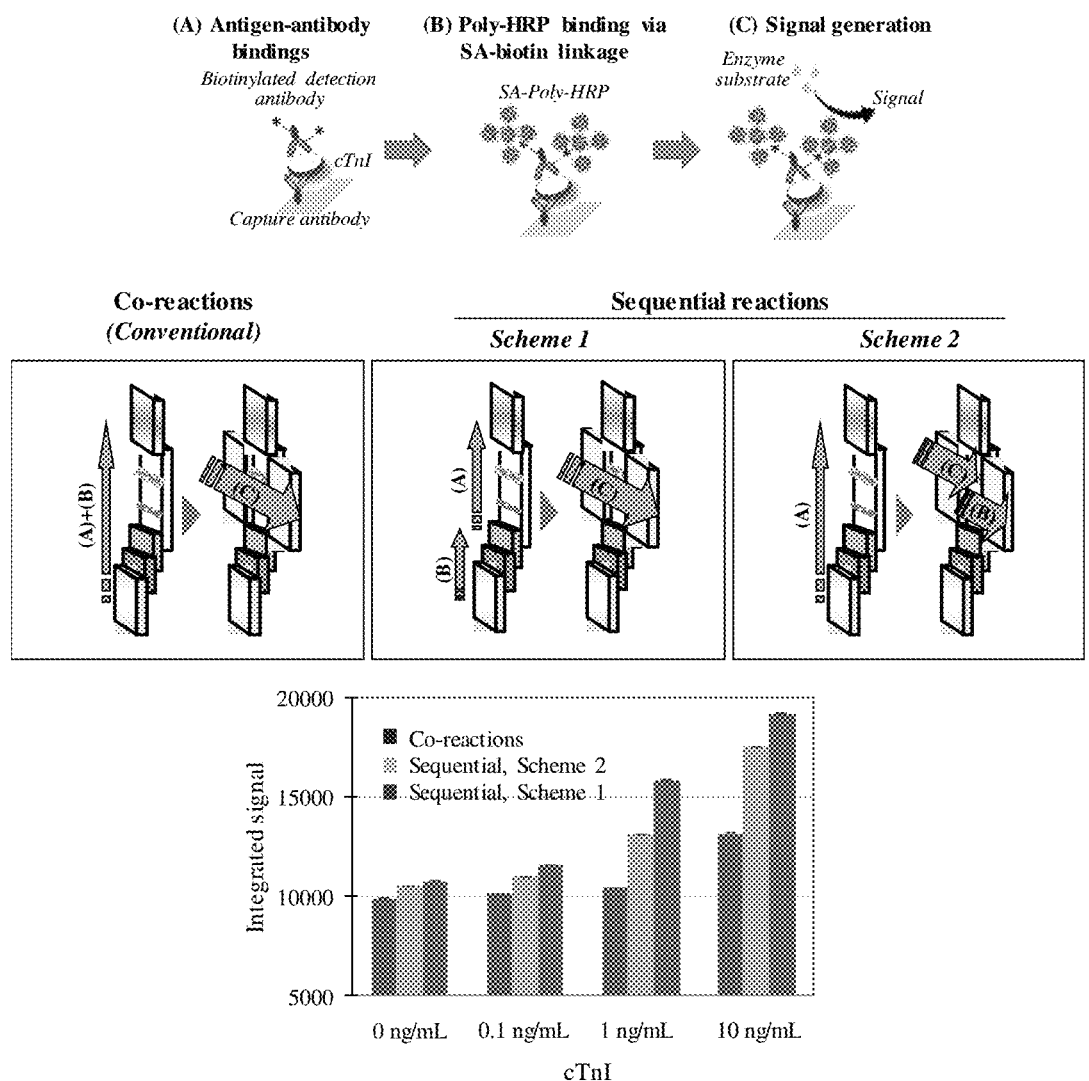
FIG. 10 shows the sequential supply control effect of the polymeric enzyme signal tracer.

Alternatively, the sandwich immune complex was formed in a vertical flow mode to thus complete Process A, and Process B was sequentially carried out in a horizontal flow mode, after which Process C for signal generation was conducted through horizontal flow as in the typical method (FIG. 10; Sequential reactions, Scheme 2). Compared to the case of Scheme 1, the signal level was slightly decreased, but the detection sensitivity was approximately consistent (FIG. 10, the bar graph colored in green). In the present invention, Scheme 2 was adopted as the method of controlling the supply of the polymeric signal tracer due to potential ease of automation.

<Example 3> Signal Generation Using Two-Dimensional Chromatography-Based Biosensor Test Example 1: Optimization of Signal Generation Conditions from Polymeric Signal Tracer Through Secondary Cross-Flow 1. Optimal Conditions for Concentration of Main Components of Biosensor Using the above modified Scheme 2 for controlling the supply of the polymeric signal tracer, the optimal concentration of a biocomponent contributing to stoichiometric signal amplification was determined. In this experiment, double-pair antibodies were used. Although the analytical time and the sample volume are important parameters for determining the analysis performance, they have to be minimized to satisfy the needs of markets and consumers. Thus, the above two parameters were fixed in this test (i.e. analytical time=15 min and sample volume<100 µL). Furthermore, the optimal conditions for signal generation, including the volume of the enzyme substrate solution and the reaction time, were the same as in the conventional method. Also, to determine the optimal concentrations of two signal generation-related components, that is, a biotinylated detection antibody and SA-Poly-HRP, under the condition that the concentration of the capture antibody was fixed, these concentrations were changed, and thus the effects on analysis performance were tested.

When only the concentration of the detection antibody was changed, the biosensor signal for a standard sample containing 0.1 ng/mL cTnI was increased proportionally to the concentration of the detection antibody in the test range used. On the other hand, the background noise in the absence of cTnI in the sample was low until the concentration of the detection antibody reached its maximum of 3 µg/mL, and then drastically increased. Consequently, the signal/noise ratio reached the maximum at the concentration of the detection antibody of about 3 µg/mL. Next, the concentration of the SA-Poly-HRP was changed, and the signal/noise ratio increased and then decreased. Thus, the optimal concentration of the polymeric signal tracer was determined to be about 0.1 µg/mL.

Test Example 2: Characterization of Analysis Performance Using Colorimetric Signal Generation The present inventors have further studied immunological sensing by generating a colorimetric signal for determining whether the analyte present in cTnI<0.01 ng/mL may be detected by the two-dimensional chromatography-based biosensor.

Figure 11:
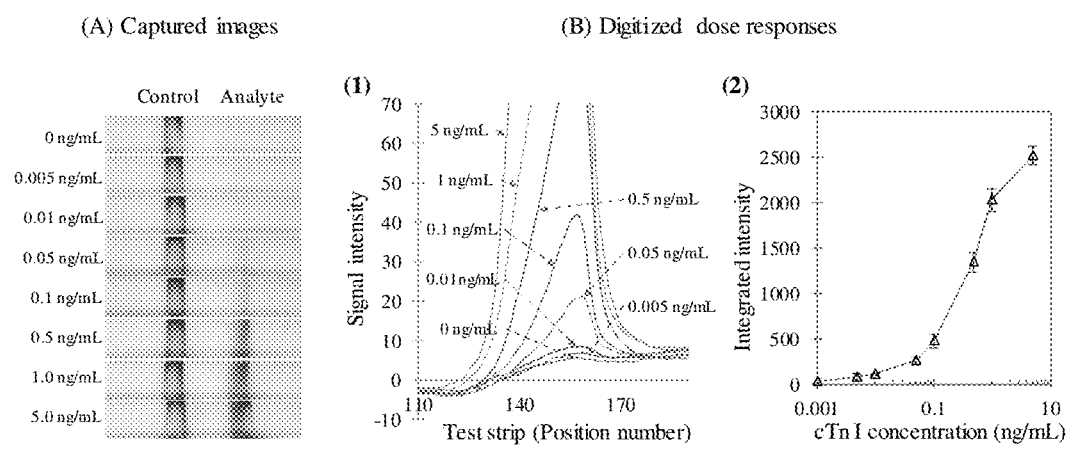
FIG. 11 shows graphs illustrating the high-sensitivity target detection of the biosensor using the polymeric enzyme signal tracer through colorimetric signal generation at the same time as washing using cross-flow.

Using the colorimetric format of the two-dimensional chromatography-based biosensor, testing was performed to obtain the dose response to only the analyte in the cTnI range of 0.005 to 5.0 ng/mL added to the human serum. As shown in sequential reaction Scheme 2 of FIG. 10, the polymeric enzyme signal tracer was sequentially supplied through horizontal flow after the antigen-antibody reaction, and the substrate solution containing the colorimetric HRP enzyme substrate (TMB) was finally supplied to generate a colorimetric signal. The color shown on the signal pad of the immuno-strip was imaged (FIG. 11, (A), colorimetric signal image), from which two signal lines, that is, an analytical line shown on the site where the capture antibody was immobilized and a control line on the site where the anti-mouse goat antibody, respectively, were obtained.

The signal level on the analytical line was proportional to changes in the concentration, whereas the control line was approximately consistent as expected. Each image was digitized to thus obtain an optical density profile in a vertical direction, which was then graphed together in an overlapping pattern (FIG. 11, (B); (1)). Since the signal value may vary depending on the image scanning position, the scanned pattern was fixed to the predetermined region. The optical density under each analytical signal curve was integrated, and the integrated signal intensity was graphed for the concentration of cTnI, thereby completing the dose-response curve (FIG. 11, (B); (2)). The dose response was closely investigated in the low concentration range, and the peak measured at 0.01 ng/mL cTnI was found to be quite different from the background noise. As mentioned above, the detection limitation obtained by multiplying the standard deviation of background noise by 3 was determined to be 0.008 ng/mL.

The sensitivity (0.008 ng/mL) of the colorimetric two-dimensional chromatography-based biosensor using the polymeric enzyme signal tracer (Poly-HRP) was increased at least ten times compared to when the existing low-molecular-weight signal tracer was used (0.1 ng/mL; refer to FIG. 5).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A two-dimensional chromatography-based biosensor, comprising:
   a cartridge comprising a vertical supply channel and a horizontal supply channel, wherein:
   the vertical supply channel comprises an immuno-strip that comprises (i) a sample addition membrane pad, (ii) a signal tracer membrane pad overlapped with the sample addition membrane pad, (iii) a signal generation membrane pad overlapped with the signal tracer membrane pad, and (iv) a vertical flow solution absorbing membrane pad overlapped with the signal generation membrane pad,
   wherein the signal generation membrane pad includes a capturing element; and the signal tracer membrane pad comprises (i) a labeling material for a signal generation and (ii) a detection element comprising a polymeric or high-molecular-weight large-sized signal tracer for detecting a binding complex formation of an analyte with the capturing element,
      wherein the polymeric or high-molecular-weight large-sized signal tracer is a material having a molecular weight of 500,000 or more or a size of 100 nm or more; and
   the horizontal supply channel extends in a direction perpendicular to the vertical supply channel, wherein the horizontal supply channel is configured to wash a remnant of the detection element after completing a first reaction of the analyte with the detection element and a second reaction of the analyte with the capturing element, thereby eliminating a noise.

2. The biosensor of claim 1, wherein the labeling material for the signal generation comprises a linker configured to achieve a direct polymerization with the detection element or a subsequent polymerization.

3. The biosensor of claim 2, wherein the polymerization is based on (i) a chemical reaction or (ii) a biological reaction selected from the group consisting of a biotin-streptavidin binding, an antigen-antibody binding, a nucleotide reaction, and a ligand-binder interaction.

4. The biosensor of claim 2, wherein the detection element includes at least one selected from an antibody, an enzyme, a receptor, a DNA, an RNA, a PNA, a protein, a carbohydrate, an inorganic material and an ion,
   wherein the antibody, the enzyme, the receptor, the DNA, the RNA, the PNA, the protein, the carbohydrate, the inorganic material and the ion specifically react with the analyte.

5. The biosensor of claim 2, wherein the labeling material for the signal generation includes one selected from the group consisting of a fluorescent signal producing material, a colorimetric signal producing material, a luminescent signal producing material, an electrochemical signal producing material, a thermal signal producing material and a magnetic signal producing material, and a combination thereof.

6. The biosensor of claim 1, wherein the capturing element comprises at least one selected from the group of an antibody, an enzyme, a receptor, an DNA, a RNA, a PNA, and a protein,
   wherein the antibody, the enzyme, the receptor, the DNA, the RNA, the PNA, and the protein specifically react with the analyte or with a complex comprising the analyte.

7. The biosensor of claim 1, wherein the horizontal supply channel comprises a horizontal flow solution absorbing membrane pad overlapped with a lateral side of the signal generation membrane pad of the vertical supply channel.

8. The biosensor of claim 7, wherein the horizontal supply channel further comprises one of (i) a washing solution supplying membrane pad for washing the remnant of the detection element left behind in the vertical supply channel after completing the first reaction of the analyte with the detection element and the second reaction of the analyte with the capturing element, (ii) a signal tracer solution supplying membrane pad for controlling a sequential supply of the detection element through the horizontal supply channel, and (iii) a substrate solution supplying membrane pad,
   wherein one of (i) the washing solution supplying membrane pad, (ii) the signal tracer solution supplying membrane pad, and (iii) the substrate solution supplying membrane pad is overlapped with the other lateral side of the signal generation membrane pad of the vertical supply channel.

9. The biosensor of claim 8, wherein the horizontal flow solution absorbing membrane pad is fixed to the lateral side of the signal generation membrane pad of the vertical supply channel, and wherein one of (i) the washing solution supplying membrane pad, (ii) the signal tracer solution supplying membrane pad, and (iii) the substrate solution supplying membrane pad is fixed to the other lateral side of the signal generation membrane pad of the vertical supply channel.

10. The biosensor of claim 8, wherein the horizontal flow solution absorbing membrane pad is detachably connected to the lateral side of the signal generation membrane pad of the vertical supply channel, and wherein one of (i) the washing solution supplying membrane pad, (ii) the signal tracer solution supplying membrane pad, and (iii) the substrate solution supplying membrane pad is detachably connected to the other lateral side of the signal generation membrane pad of the vertical supply channel.

11. The biosensor of claim 8, further comprising a tank that is in fluid communication with one of (i) the washing solution supplying membrane pad, (ii) the signal tracer solution supplying membrane pad, and (iii) the substrate solution supplying membrane pad.

* * * * *